US005559431A

United States Patent [19]

Sellen

[11] Patent Number: 5,559,431
[45] Date of Patent: Sep. 24, 1996

[54] METHOD OF CALIBRATING A SENSOR

[75] Inventor: Martin Sellen, Merzig, Netherlands

[73] Assignee: Micro-Epsilon Messtechnik GmbH & Co. KG, Ortenburg, Germany

[21] Appl. No.: 319,882

[22] Filed: Oct. 7, 1994

[30] Foreign Application Priority Data

Oct. 8, 1993 [DE] Germany ............ 43 34 380.5

[51] Int. Cl.$^6$ .................. G01R 35/02; G01N 27/72; G01G 23/48
[52] U.S. Cl. ............. 324/202; 324/225; 364/571.01
[58] Field of Search ............... 324/202, 228, 324/234, 239–243, 235–237, 225; 364/571.01–571.07; 73/1 R, 1 J

[56] References Cited

U.S. PATENT DOCUMENTS

| | | | |
|---|---|---|---|
| 4,390,949 | 6/1983 | Beningfield et al. | 364/429 |
| 4,673,870 | 6/1987 | Strickland et al. | |
| 4,771,237 | 9/1988 | Daley | 324/202 |
| 5,311,125 | 5/1994 | Krause et al. | 324/201 |
| 5,394,084 | 2/1995 | Snyder | 324/202 |

FOREIGN PATENT DOCUMENTS 3116690  11/1982  Germany.

Primary Examiner—Sandra L. O'Shea
Assistant Examiner—Roger Phillips
Attorney, Agent, or Firm—Bell, Seltzer, Park & Gibson, P.A.

[57] ABSTRACT

To suppress and compensate influences of disturbance variables, a method of calibrating a sensor is disclosed, in which at most as many so-called influence variables influencing the measuring result are considered as measurable quantities are detected by the sensor, the set of the influence variables being composed of at least one disturbance variable influencing the measurement and at least one target quantity to be determined from the measurable quantities. The method in accordance with the invention is characterized in that several values of the target quantity and several states characterized by the disturbance variable are defined, that for all combinations of defined values of the target quantity with defined states the corresponding values of the measurable quantities are acquired, that from one each of the defined values of the target quantity and the corresponding values of the measurable quantity respectively a set of coefficients is determined for all defined states, and that the sets of coefficients are associated each to the corresponding value of the target quantity and stored.

18 Claims, 4 Drawing Sheets

METHOD OF CALIBRATING A SENSOR

BACKGROUND OF THE INVENTION

The present invention relates to a method of calibrating a sensor, in which at most as many so-called influence variables affecting the measuring result are considered, as measurable quantities are detected by the sensor, the set of the influence variables being composed of at least one disturbance variable influencing the measurement and of at least one target value which is to be determined from the quantities being measured. The present invention relates in particular to a method of calibrating an eddy-current sensor for distance measuring and for material testing.

For measuring nonelectrical, primarily mechanical quantities, modern automated manufacturing processes make increasing use of electronic sensors as control sensors, in particular noncontacting distance sensors. Besides the almost nonreactive detection of the measurable quantities, further advantages of such sensors lie in a response practically free of delay, in the insensitivity to vibrations, dust, moisture, and chemically aggressive vapors, as well as in the extensive freedom from maintenance.

Important representatives of this group are the eddy-current sensors, which are especially suitable for measuring short displacements and distances under difficult environmental conditions. Similarly to the instance of a plurality of other measuring methods, in the instance of distance measuring by means of the eddy-current measuring principle, the quantities being measured (i.e., measurable quantities) include the resistive (R) and reactive (X) components of the impedance (Z) of the object of measurement (i.e., the target). The resistive and reactive components are influenced not only by the target quantity, the distance, but are to the same extent dependent on a whole series of other influence variables such as the conductivity ($\sigma$) and/or permeability ($\mu$) of the target. Besides the factors which are known in the measurement or are adjustable, such as, for example, the geometry of the coil and object of measurement, frequency and amplitude of the coil current, the influences of mostly unknown material properties of the object being measured create the greatest problems. Examples are primarily inhomogeneities in the conductivity and permeability, as well as temperature fluctuations and material defects. The conductivity and permeability of the object of measurement or the target are hereafter described as disturbance variables.

It is the object of the present invention to provide a method of calibrating any desired sensor, such as an eddy-current sensor, so as to suppress disturbance variables.

SUMMARY OF THE INVENTION

The above and other objects and advantages of the present invention are achieved by a method of calibrating a sensor wherein several values of the target quantity and several values of the influence variable or variables, hereinafter referred to as states, are initially defined. For all combinations of defined values of the target quantity with defined states, the corresponding values of the quantities being measured are acquired. Finally, from each of the defined values of the target quantity and the corresponding values of the quantities being measured, one set of coefficients each is determined for all defined states. As a result, as many sets of coefficients are obtained as there are defined values of the target quantity. These sets of coefficients are associated each to the corresponding value of the target quantity and stored.

In accordance with the invention, it has been recognized that the thus-determined sets of coefficients reflect the influence of changes in the disturbance variables on the quantities being measured, and that the disturbance variables can be eliminated with the aid of the determined sets of coefficients and a special processing of the measured data.

Prerequisite for such a calibration is the presence of at least as many measurable quantities as there are influence variables to be considered. If the sensor to be calibrated is operated by ac voltage, it will be possible to realize in advantageous manner additional measurable quantities by operating the sensor at different calibrating frequencies in the so-called multifrequency or pulse method.

To supplement the method of calibrating a sensor and of processing the measured data in accordance with the invention, i.e., to determine an unknown value of the target quantity, it is proposed to first acquire the values of the quantity being measured, which correspond to the unknown value of the target quantity. These acquired values of the quantity being measured are then offset against the stored sets of coefficients, in that the acquired values of the quantity being measured are multiplied with each of the stored sets of coefficients, and are added each to a subtotal, the subtotal being associated to the same defined value of the target group as the respective set of coefficients. Thereafter, a range of values between two successive values of the target quantity can be determined as a range of values for the unknown target quantity, with the deviation from the corresponding subtotal being positive for one of these two defined values of the target quantity.

In a further step of the evaluation, the differences between the defined values of the target quantity and the corresponding subtotals are interpreted as values of an error function that is dependent on the target quantity. The unknown value of the target quantity may then be estimated as the value of the target quantity at the zero passage of the error function.

There are now various possibilities of determining the zero passage of the error function. Methods lending themselves therefor are either the method of interpolation or the method of approximation. These methods furnish differently good results, and differ from one another very greatly in the necessary computing expenditure. A further quality criterion, which matters in particular in the interpolation process, is the waviness of the functions between the points of support. As a direct method a linear interpolation of the error function is suggested, in which the individual points of support are interconnected by line segments. Since only the zero passage of the piecewise defined linear function is of interest, it suffices to consider only the two points of support, between which a change in signs occurs. The computation of the zero value is absolutely no problem in this instance.

Another possibility, which is however substantially costlier, is the so-called spline interpolation of the error function. Likewise in this instance, the error function is defined in segments. Between two support points each, a polynomial of, for example, the third degree is placed so that neighboring polynomials match at the common support point in the functional value and in the derivatives. As a function of the desired solution, it does here not suffice to observe only the interval, in which the zero passage lies. Good results were also obtained with three additional intervals each above and below the zero passage, namely with eight support points. The zero point determination may occur via a direct method of calculation for third degree-polynomials, or however by a numerical method, for example the Newton's method. As a beginning value, the result of the already described linear method may be used. As a result of the special construction of the splines it has shown to be useful to add one support point each at the interval limits of the measuring range. This allows to ensure a smooth shape of the curve in the entire measuring range. In summary, it can be stated that an interpolation process is to be preferred always, when one can presume that the received measuring data are noisefree. Otherwise, a method of approximation is to be preferred. The advantages of the linear interpolation lie in the very simple and fast computation of the curve parameters and the point of the zero passage. The computing expenditure is substantially higher with the spline interpolation. The maximum error in estimating the unknown value of the target quantity instead is however also smaller by the factor 5 in comparison with the linear interpolation. An approximation of the error function could be performed, for example, in the meaning of the smallest squares of error.

The above generally described method of calibration, namely for any desired sensor, and the processing of measured data described in connection therewith, will be described in the following again by the specific example of calibrating an eddy-current sensor having at least one measuring coil. Used as the measurable quantities are this instance the real and the imaginary part of the coil impedance at different frequencies. These measurable quantities are dependent on many influence variables. All geometric dimensions and basic electrical data of the sensor are fixed quantities and are, therefore, not included as influence variables in the calibration process. It is further presumed that the surface of the used target is flat, parallel to the sensor, and large enough relative to the sensor diameter. In addition, the targets should have a thickness, which is greater than the depth of penetration of the eddy currents. Further, the targets are to be free from surface defects. Three essential influence variables now remain for the calibration, with the spacing d between the sensor and the target representing the target quantity to be described, and the electrical conductivity and the effective permeability representing the disturbance variables to be suppressed. It is therefore necessary to give special consideration to these disturbance variables, since material defects as well as changes in temperature largely result in fluctuations of the electrical conductivity and effective permeability, or entail like changes in measurement as same.

In accordance with the invention, several distance values $d_i$ and several states characterized by the electrical conductivity and the effective permeability of the target, or combinations of states $ZK_j$ are now defined, their values being selected each from physically useful ranges. For the distance d, it is the selected measuring range. For the combinations of states ZK, these are the expected ranges of the electrical conductivity and the permeability. Now, the corresponding measurable quantities $M_l$ are acquired for all combinations of distance values $d_i$ with combinations of states $ZK_j$. Then, from one each of the distance values $d_i$ and the corresponding values of measurable quantity $M_l$, a set of coefficients $k_l$ is determined for all combinations of state $ZK_j$. The thus determined sets of coefficients $k_j$ are then associated each to the corresponding distance values $d_i$ and stored for a later processing of the measuring data.

If one includes for a certain distance d a total of m measured values, namely the real and imaginary parts of the coil impedance at m half frequencies with a fixed combination of states ZK, the distance d is calculated as sum $$d = k_1 \overline{M}_1 + k_2 \overline{M}_2 + \ldots + k_m \overline{M}_m.$$

If one performs now this measurement for the fixed distance d and k different combinations of states ZK, k equations will be available to determine m unknown coefficients. In this manner, it is possible to determine the sets of coefficients $k_j$ with a corresponding selection of k of the number of states or combinations of states ZK, and of m of the number of measurable quantities.

If a distance measurement occurs with a sensor calibrated in such a manner, the distance estimate will be divided into several steps. First, with the aid of the measuring data $\overline{mx}_m$ which are acquired for the unknown distance d to be determined, an error value $\Phi(d_i)$ according to the equation $$\Phi(d_i) = K_{m,i} \cdot \overline{mx}_m - d_i$$

is associated to each calibration distance, i.e. to each of the defined distance values $d_i$.

In a second step, a function $\Phi(d)$ is produced from these points by interpolation or approximation. The point $d_x$, at which this function has its zero passage, represents a good estimate of the distance d being sought. The accuracy of the distance estimation depends essentially on the quality of the calculated sets of coefficients $k_j$.

The above-described method of calibration permits distance measurements right to the micrometer range and irrespective of the fluctuations of the electrical conductivity and the effective permeability. Prerequisite therefor are, as aforesaid, the determination of good sets of coefficients and the correct evaluation of the acquired measuring data. In the following, advantageous embodiments of this method are described, and in particular the effects of different parameter selections are explained.

It has shown to be especially advantageous to use at least six measurable quantities $M_l$, i.e. the real and the imaginary part of the impedance of the measuring coil, with at least three different calibration frequencies, since tests have resulted in that a resolution of less than 10 micrometers can be obtained.

The selection of the combinations of states ZK has in a two-fold respect an influence on the error of estimation for an unknown target quantity that is to be determined, such as, for example, the distance d. Important are in this connection, on the one hand, their distribution over the expected ranges of the disturbance variable, and on the other hand their number k. Since the relationships between disturbance variables and measurable quantities are not linear, it is advantageous to distribute the combinations of states nonuniformly over the expected ranges. Especially advantageous is, when more of the defined combinations of states lie in the ranges of lower electric conductivities and effective permeabilities than in the ranges with higher values. To achieve satisfactory measuring results it is further of advantage, when the number k of the defined combinations of states ZK is selected larger than twice the number of the used calibration frequencies. The optimal selection of the number k depends quite substantially on the number and quantity of the calibration frequencies. At higher frequencies, lesser combinations of states will do than at lower frequencies. Basically, one should try a smallest possible number k of defined combinations of states ZK, since in a technical conversion of this method, the calibration expenditure will rise considerably with an increasing k.

It is possible to achieve a decrease in the estimation error in the calibration not only by including additional defined combinations of states ZK, but also by closer calibration intervals, i.e. by an increase in the number of defined distance values $d_i$. Contrary to the defined combinations of states ZK, it is possible to select the defined distance values $d_i$ equidistant.

With respect to the acquisition and evaluation of measuring data, it should be pointed out that the constancy of the measuring frequencies is very important for a good measuring result. The measuring frequencies must correspond exactly to the fixed calibration frequencies, since even small deviations will entail high error values. Thus, for example, a fluctuation of only 0.5% of the desired values leads to an increase of the error by more than the factor 50.

Finally, it should be remarked that as a result of the calibration in accordance with the invention, an eddy-current sensor may be used also for material testing with the advantage of distance independence, when the electrical conductivity and the effective magnetic permeability of the target material are assumed as target quantities, and the spacing between the sensor and the target surface as the disturbance variable. Such a material testing could consist of, for example, testing the homogeneity of the target material or also of detecting damage in the surface structure of a target.

There exist various possibilities of perfecting and further developing the subject matter of the present invention in an advantageous manner. To this end, reference may be made to the following description of embodiments of the invention with reference to the drawing. In combination with the description of the preferred embodiments of the invention with reference to the drawing, also generally preferred embodiments of the teaching are explained.

DETAILED DESCRIPTION OF THE PREFERRED EMBODIMENTS

Figure 1:
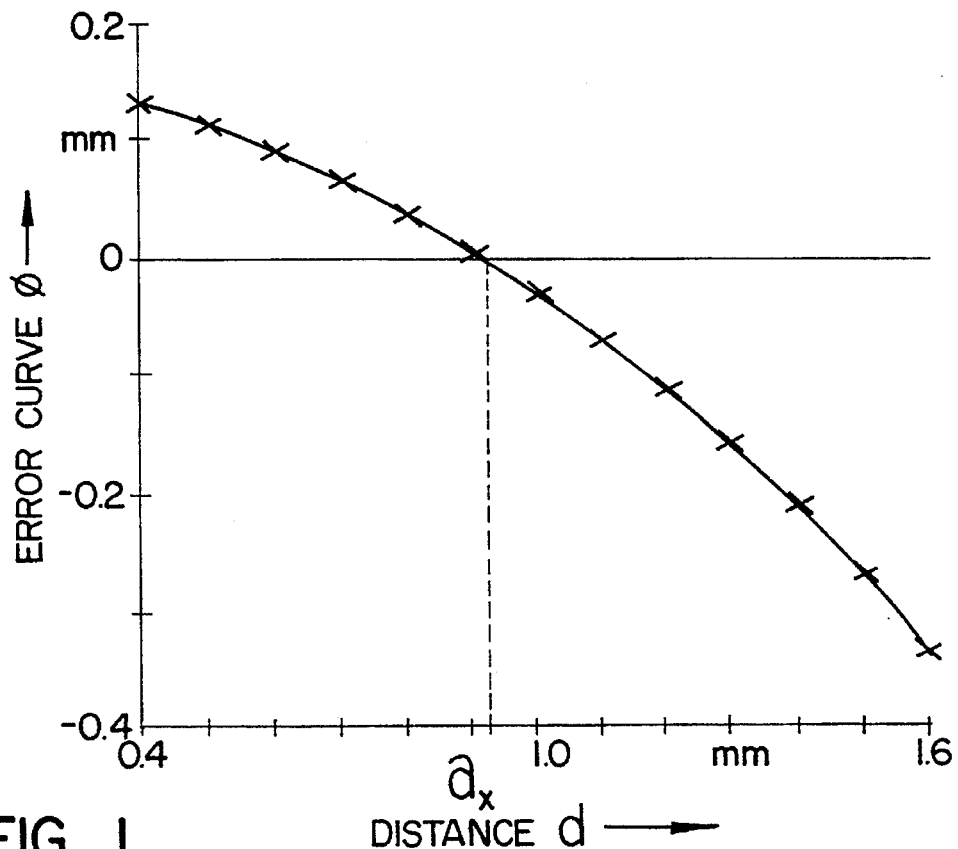
FIG. 1 shows the curve of an error function $\Phi$(of d) as determined in accordance with the invention by way of the example of a distance measurement with d =0.921 mm.

All Figures relate to distance measurements which were conducted by way of example for test purposes by means of an eddy current sensor that was calibrated in accordance with the invention. FIG. 1 shows the curve of an error function $\Phi(d)$ that was determined by means of a method of approximation or interpolation. Such an error function may be determined by the method described in the general part of the specification based on the acquisition of measuring data for an unknown distance that is to be determined. The distance to be determined results then as a zero passage of the error function $\Phi(dd)$, in this instance, in $d_x$=0.921 mm.

Figure 2:
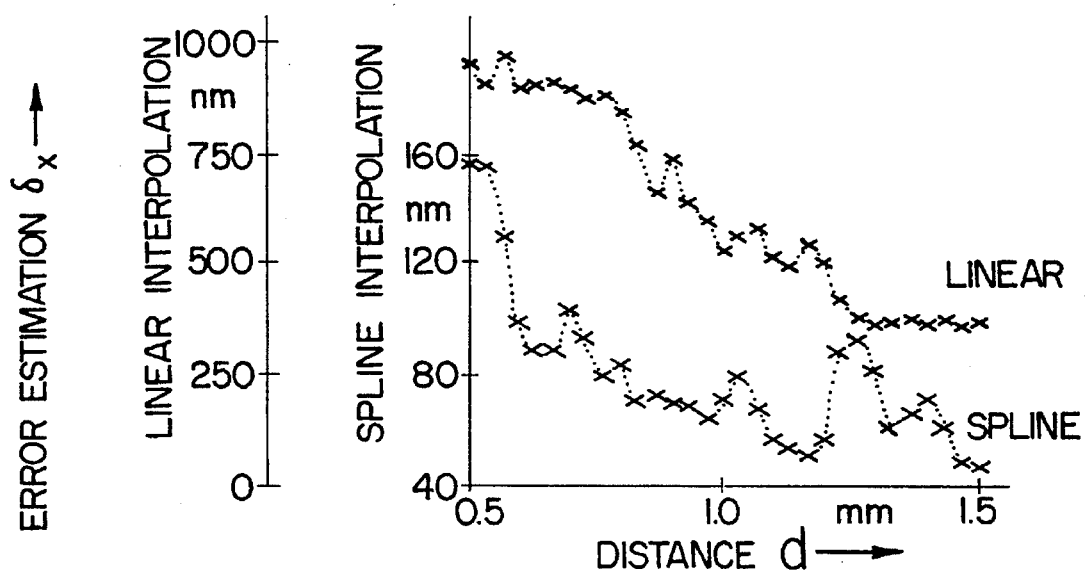
FIG. 2 shows the influence of the interpolation method on the error in estimating.

Shown in FIG. 2 is the influence of the method selection by the example of a comparison between linear interpolation and spline interpolation of the error function $\Phi(d)$. Both for the calibration and the determination of distance, simulated values were used at the frequencies of 0.3 MHz, 0.6 MHz, 1.2 MHz, and 2.4 MHz. In the range from 0.5 mm to 1.5 mm the error in estimating was determined for 33 different distances with both methods of interpolation.

Figure 3:
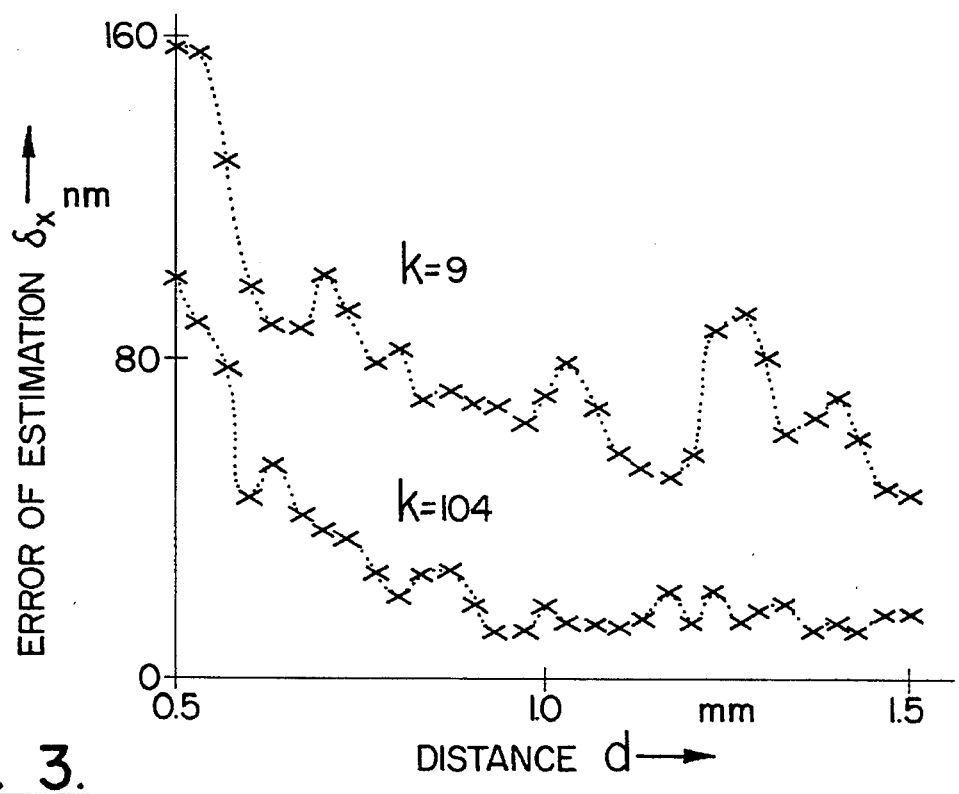
FIG. 3 shows the influence of number k of defined combinations of states on the error in estimating.

In FIG. 3, the same calibration data were used as in FIG. 2. Furthermore, the spline interpolation was employed. The two curves show that an increase in the number of the defined combinations of state by the factor 12 causes an average decrease of the estimation error by the factor 2.

Figure 4:
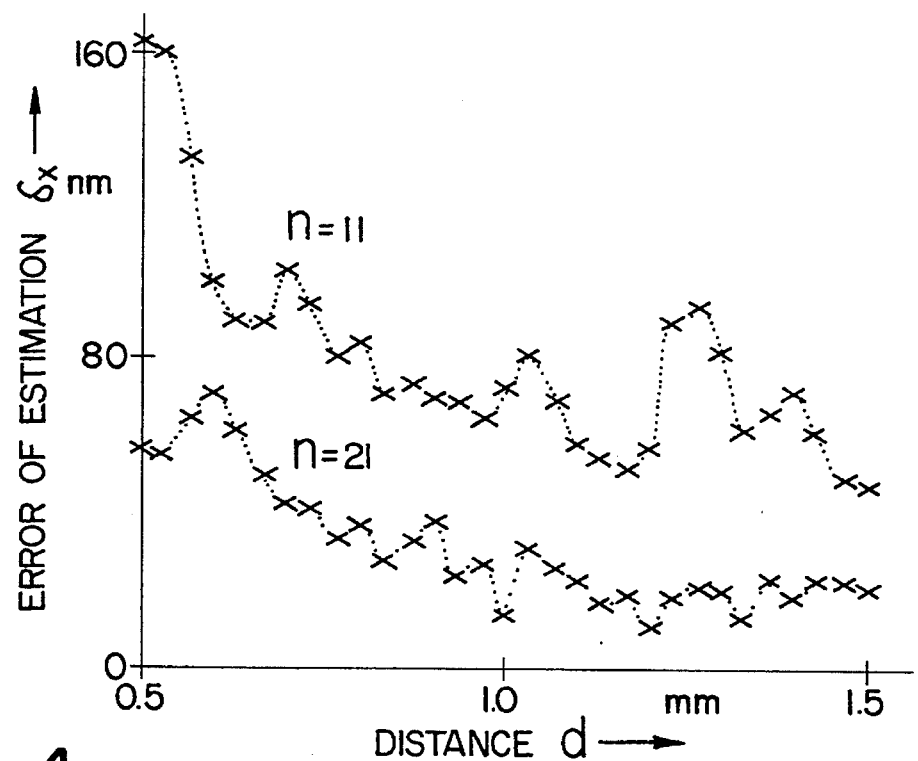
FIG. 4 shows the influence for the number n of defined distance values $d_i$ on the error in estimating.

FIG. 4 illustrates by two curves with equidistant calibration intervals, that also the selection of closer calibration intervals, i.e., and increase in the number n of the defined distance values $d_i$, results in a decrease of the estimation error. In both cases, the number k of the combinations of states was selected to be nine, and the spline interpolation was chosen. It can be seen, that the division in half of the distance interval, which corresponds to a doubling of the number n of the defined distance values $d_i$, leads to an average decrease of the estimation error by the factor 1.7.

In this connection, it should be remarked that the measuring results, which can be obtained by a sensor calibrated in accordance with the invention, depends to a particular degree on the structure of the measuring coil. It is necessary that the measuring coil and the measuring technique guarantee very accurate measurements of the coil impedance, since the calibration method as presented is very sensitive to measuring data fluctuations. If a coil impedance changes by 0.03% during a measuring, same may lead to an inaccuracy of measurement of 0.1% of the measuring result. This characteristic of the method sets high demands to the coil and measuring technique with respect to a very effective compensation for temperature and parasitic influences.

To be able to also document the effectiveness of the calibration method in accordance with the invention in the suppression of great fluctuations of disturbance variables, the following experiment was made. Used for calibrating and measuring was an exploring coil with the dimensions:
Outside radius: 3.81 mm
Inside radius: 3.00 mm
Coil height: 0.63 mm
Self-inductance: 31.37 µH
Resistance at 200 kHz: 5.31 Ω

Ten combinations of states ZK were employed for the calibration at the four frequencies of 200 kHz, 400 kHz, 1 MHz, as well as 2 MHz. Selected as calibration intervals, i.e. defined distance values were 0.3 mm, 0.4 mm, . . . , 3.0 mm, 3.2 mm, i.e., n=30. Ten materials of the following table were employed as targets, with aluminum having been used only for the measurements.

| Material | Material Number | Electric Conductivity $m/\Omega mm^2$ (20° C.) |
| --- | --- | --- |
| Iron 2N+ | 1 | 10.3 |
| Copper 2N | 2 | 60 |
| Magnesium | 3 | 22.4 |
| Brass | 4 | 14.2 |
| Molybdenum 3N5 | 5 | 19.4 |
| Nickel 2N5 | 6 | 14.6 |
| Niobium 2N8 | 7 | 7.6 |
| V2A9 Steel | 8 | 9.1 |
| Zinc 4N | 9 | 16.9 |
| Tin 2N8 | 10 | 8.7 |
| Aluminum | 11 | 37.6 |

Figure 5:
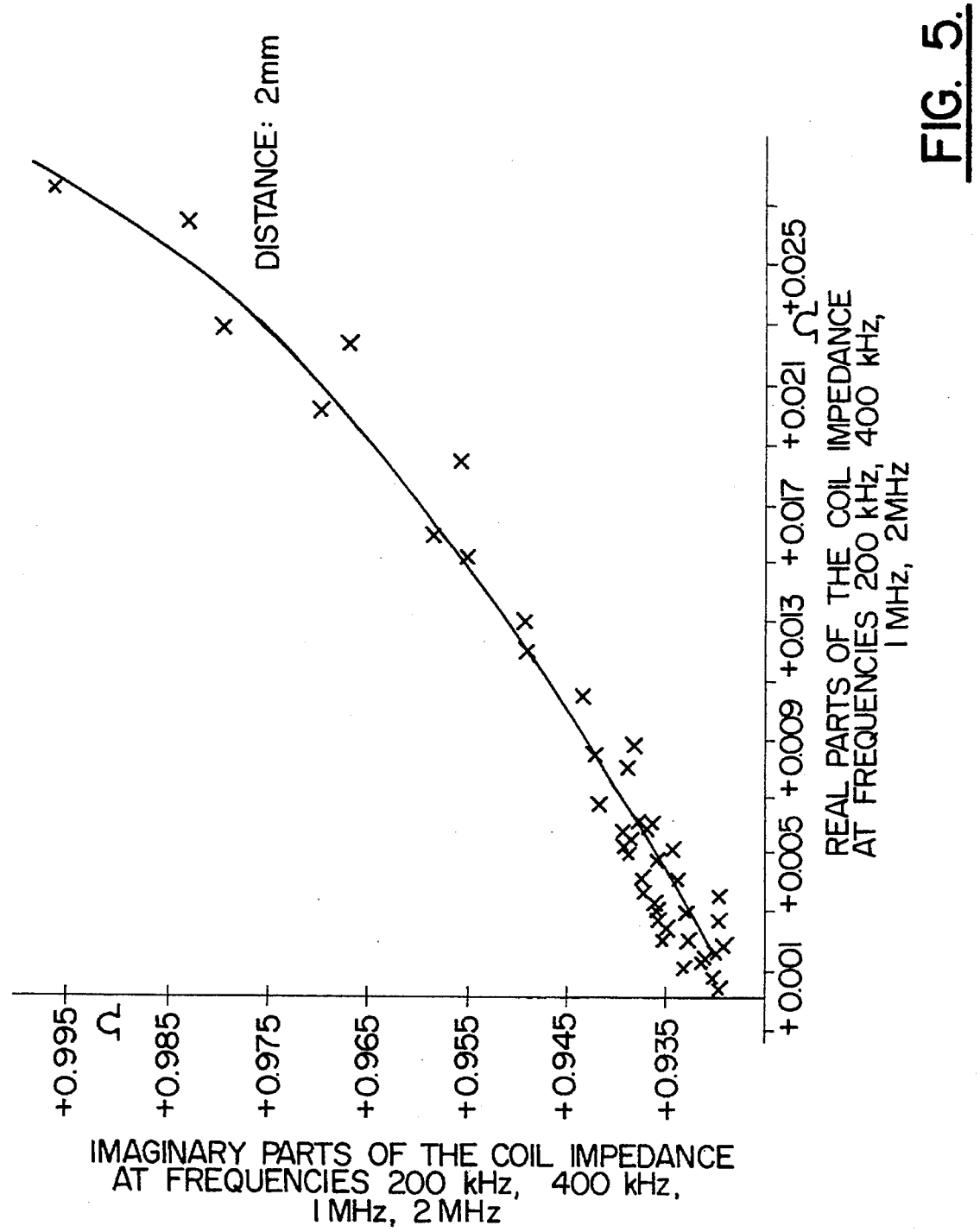
FIG. 5 shows a determination of a set of calibration coefficients.

For each of the thirty calibration intervals, a set of coefficients was computed. Shown in FIG. 5 is the operating mode of these sets of coefficients by the example of a calibration interval of d=2 mm. With the aid of the four frequencies and the ten targets, forty calibration points indicated at "x" are generated. The set of coefficients pertaining to this particular calibration interval defines an optimal curve through these points, which reflects the response of the sensor at this distance. Theoretically, the points must lie along this curve. The fact that this is not so, is caused in that the zero point, at which the spacing between the sensor and the target is zero, was not approached automatically, but by hand, and that the capacitance of the supply cable was not adequately compensated. Such measuring errors interfere greatly with the calibration, which can also be read in the result of the measurement.

Figure 6:
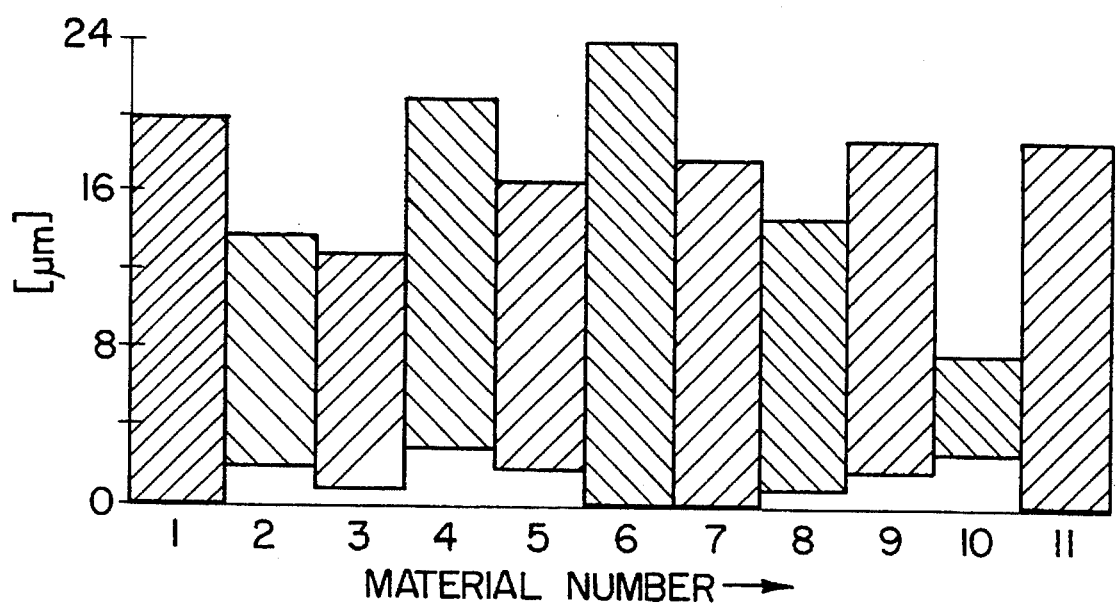
FIG. 6 shows error ranges of eleven selected targets over a measuring range.

With the calibrated sensor, measurements were conducted against all targets of the table. The interval from 0.5 mm to 3.0 mm was established as measuring range. Within this interval, measuring data were acquired every 50 µm at the four frequencies, which were used to estimate the respective distance. FIG. 6 shows the result of these estimations. Plotted for the eleven targets is the range, which covers the deviations or the error in estimating for all measured distances. The maximum error of estimation of 24 µm over all measurements resulted for nickel at a measuring distance of 1.85 mm. This means that despite the nonoptimal calibration measurements, a determination of the distance was achieved with an accuracy to 50 µm over the entire measuring range and regardless of the target material.

Finally, it should be noted that the teaching of the present invention has been described above only by the example of an eddy-current sensor. However the teaching of this invention is not limited to the application in connection with an eddy-current sensor, but may also be realized in principle with other types of sensors.

That which is claimed:

1. A method of calibrating a sensor, in which at most as many influence variables affecting the measuring results are considered as measurable quantities are detected by the sensor, the number of influence variables being composed of at least one disturbance variable influencing the measurement and at least one target quantity to be determined from the measurable quantities, and comprising the steps of:

defining several values of the at least one target quantity and defining several values of the at least one disturbance variable for each of the defined values of the at least one target quantity;

detecting the corresponding values of the measurable quantities for all combinations of defined values of the at least one target quantity with corresponding defined Values of the at least one disturbance variable;

determining from each of the defined values of the at least one target quantity and the corresponding detected values of the measurable quantities a respective set of coefficients;

associating each of the sets of coefficients to the corresponding defined values of the at least one target quantity; and storing the sets of coefficients, wherein for determining an unknown value of the at least one target quantity the corresponding values of the measurable quantities are detected, wherein the detected values of the measurable quantities for the corresponding unknown value of the at least one target quantity are multiplied with each of the stored sets of coefficients and added up to a subtotal for each set of coefficients, the subtotal being associated to the same defined value of the at least one target quantity as the respective set of coefficients, and that a range of values between two successive defined values of the at least one target quantity is determined as a range of values for the unknown target quantity, the deviation from the corresponding subtotal being positive for one of these two defined values of the at least one target quantity, whereas the deviation from the corresponding subtotal is negative for the other of these two defined values of the at least one target quantity.

2. The method as in claim 1, the differences between the defined values of the at least one target quantity and the corresponding subtotals are interpreted as values of an error function dependent on the at least one target quantity, and that the unknown value of the at least one target quantity is estimated as the value of the at least one target quantity at the zero passage of the error function.

3. The method as in claim 2, wherein an interpolation of the error function is carried out to determine its zero passage.

4. The method as in claim 3, wherein a linear interpolation of the error function is carried out to determine its zero passage.

5. The method as in claim 3, wherein a spline interpolation of the error function is carried out to determine its zero passage.

6. The method as in claim 2, wherein an approximation of the error function is carried out to determine its zero passage.

7. The method as in claim 6, wherein an approximation is carried out in the meaning of the smallest error squares.

8. A method of calibrating a sensor, in which at most as many influence variables affecting the measuring results are considered as measurable quantities are detected by the sensor, the number of influence variables being composed of at least one disturbance variable influencing the measurement and at least one target quantity to be determined from the measurable quantities, and comprising the steps of:

defining several values of the at least one target quantity and defining several values of the at least one disturbance variable for each of the defined values of the at least one target quantity;

detecting the corresponding values of the measurable quantities for all combinations of defined values of the at least one target quantity with corresponding defined values of the at least one disturbance variable;

determining from each of the defined values of the at least one target quantity and the corresponding detected values of the measurable quantities a respective set of coefficients;

associating each of the sets of coefficients to the corresponding defined values of the at least one target quantity; and storing the sets of coefficients;

wherein said sensor is an eddy current sensor having at least one measuring coil, with the distance d between the eddy current sensor and a target forming the at least one target quantity, the electric conductivity and the effective permeability of the target forming the at least one disturbance variable, and the real and imaginary parts of the impedance of the measuring coil at different frequencies being acquired as measurable quantities $M_l (l=1, \ldots, m)$ and wherein several distance values $d_i (i=1, \ldots, n)$ and several values $ZK_j (j=1, \ldots, k)$ of the electric conductivity and the effective permeability of the target are defined, wherein for all combinations of distance values $d_i$ with combinations of values $ZK_j$ the corresponding measurable quantities $M_l$ are detected, wherein from each one of the distance values $d_i$ and the corresponding values of measurable quantities $M_l$ for all combinations of values $ZK_j$ a set of coefficients $k_i$ ($k_i=(k_{i1}, \ldots, k_{im})$) is determined, and that the sets of coefficients $k_i$ are associated each to the corresponding distance value $d_i$ and stored.

9. The method as in claim 8, wherein at least six measurable quantities $M_l$ are used ($m \geq 6$), i.e., the real and imaginary parts of the impedance of the measuring coil are detected at at least three different calibration frequencies.

10. The method as in claim 8, wherein the combinations of values $ZK_j$ are selected from an expected range of physically useful combinations of values, and that more combinations of values $ZK_j$ are selected from the ranges of low electric conductivities and effective permeability than from ranges of higher electric conductivities and effective permeabilities.

11. The method as in claim 8, wherein the number k of combinations of values $ZK_j$ is selected larger than twice the number of employed calibration frequencies.

12. The method as in claim 8, wherein the number k of combinations of values $ZK_j$ is selected all the smaller the higher the employed calibration frequencies are.

13. The method as in claim 8, wherein the distance values $d_i$ are selected equidistant.

14. The method as in claim 8, characterized in that for improving the measuring result the number n of distance values $d_i$ is increased.

15. The method of detecting and evaluating the measuring data of a sensor calibrated as in claim 8 wherein the detection of the measurable quantities for determining the sets of coefficients $k_i$ is carried out at the same measuring frequencies as the detection of the measurable quantities for determining the distance d.

16. A method of calibrating a sensor, in which at most as many influence variables affecting the measuring results are considered as measurable quantities are detected by the sensor, the number of influence variables being composed of at least one disturbance variable influencing the measurement and at least one target quantity to be determined from the measurable quantities, and comprising the steps of:

defining several values of the at least one target quantity and defining several values of the at least one disturbance variable for each of the defined values of the at least one target quantity;

detecting the corresponding values of the measurable quantities for all combinations of defined values of the at least one target quantity with corresponding defined values of the at least one disturbance variable;

determining from each of the defined values of the at least one target quantity and the corresponding detected values of the measurable quantities a respective set of coefficients;

associating each of the sets of coefficients to the corresponding defined values of the at least one target quantity; and storing the sets of coefficients;

wherein said sensor is an eddy-current sensor having at least one measuring coil, wherein the distance d between the eddy current sensor and a target is considered as the at least one disturbance variable, the electric conductivity and the effective permeability of the target form the at least one target quantity, and the real and imaginary parts of the impedance of the measuring coil are detected at different frequencies as measurable quantities $M_l$ ($l=1, \ldots, m$).

17. The method as in claim 16, wherein it is employed for testing the target material.

18. The method as in claim 16, wherein the method is employed for testing the homogeneity of the target material or for detecting damage in the structure of the surface of a target.

* * * * *